United States Patent [19]

Felman et al.

[11] Patent Number: 5,827,700

[45] Date of Patent: Oct. 27, 1998

[54] PROCESS FOR PRODUCING CITRIC ACID FROM AN IMPURE PROCESS STREAM

[75] Inventors: Steven W. Felman, Granger, Ind.; Chetna Patel, Naperville, Ill.; Bhalchandra H. Patwardhan, Granger; David J. Solow, Elkhart, both of Ind.

[73] Assignee: Bayer Corporation, Elkhart, Ind.

[21] Appl. No.: 922,094

[22] Filed: Sep. 2, 1997

Related U.S. Application Data

[63] Continuation of Ser. No. 460,140, Jun. 2, 1995, Pat. No. 5,712,131, which is a continuation-in-part of Ser. No. 88,219, Jul. 6, 1993, abandoned.

[51] Int. Cl.$^6$ .................................. C12P 7/40; C12P 7/48
[52] U.S. Cl. ............................................. 435/144; 435/136
[58] Field of Search ...................................... 435/136, 144

[56] References Cited

U.S. PATENT DOCUMENTS

| 4,994,609 | 2/1991 | Baniel et al. | 562/580 |
| 5,032,686 | 7/1991 | Duflot et al. | 562/580 |
| 5,034,105 | 7/1991 | Bergland et al. | 204/182.4 |

OTHER PUBLICATIONS

Jutten, "Enhanced Crystallization of Dicarboxylic acids . . . ", pp. 1–66, abstr. also, 1992.

*Primary Examiner*—David M. Naff
*Assistant Examiner*—Deborah K. Ware

[57] ABSTRACT

The disclosed invention provides for two improved processes for recovering citric acid and other organic acids. The process for recovering citric acid from an impure process stream includes concentrating the impure process stream to obtain a concentrated solution of citric acid, adding a sufficient amount of a strong acid or salt to the solution in order to crystallize citric acid and separating the resulting citric acid crystals from the mother liquor. The useful strong acids or salts thereof are sulfuric acid, hydrochloric acid, sodium chloride, sodium sulfate and nitric acid. Also ion exchange resins may be utilized in order to recover additional yields of citric acid. Further, the impure process stream is obtained by a solvent extraction process or a lime and sulfuric acid process. The other useful process provided for by the invention includes recovering organic acid from an impure process stream, such as a fermentation broth. However, the acid is added to the impure process stream in the first step and then concentrating the resulting impure process stream to recover crystals from the concentrate thereof. This particular improved process is essentially one step purification without the waste disposal problems or large capital investment required by either the conventional lime/sulfuric or solvent extraction recovery processes.

6 Claims, No Drawings

PROCESS FOR PRODUCING CITRIC ACID FROM AN IMPURE PROCESS STREAM

This is a continuation of application Ser. No. 460,140, filed on Jun. 2, 1995, now U.S. Pat. No. 5,712,131 which in turn was a continuation-in-part of application Ser. No. 088,219 filed Jul. 6, 1993, now abandoned.

BACKGROUND OF THE INVENTION

Production of an organic acid, such as citric acid, by fermentation is well known and is practiced on a commercial basis throughout the world. In particular, citric acid is produced commercially primarily by an aerobic fermentation process, which employs molasses, starch, or a sugar, such as glucose, fructose, sucrose, or converted lactose, as a substrate and a fungus, such as Aspergillus niger, or yeast, such as Candida lipolytica, as a biocatalyst. In the typical fermentation process residual liquor from the product stream is usually recycled back into the process. Over time, this results in a build up of significantly high levels of impurities. The fermentation product typically contains substantial amounts of impurities, including biomass from the spent microorganism, carbohydrates, amino acids, proteins and salts, as well as citric acid, which must be separated from the fermentation broth to provide a pure product. The present invention provides a simple and commercially practical process for the recovery of pure organic acid from an impure fermentation broth.

Two principal techniques are used at this time to separate the citric acid from the impurities generated during fermentation: a lime/sulfuric acid process and solvent extraction process.

In the so-called lime/sulfuric acid process fermentation broth is first subjected to a "liming" operation which involves a treatment with calcium hydroxide and the resulting calcium citrate is filtered off, washed, and then decomposed with aqueous sulfuric acid. The calcium sulfate that forms is filtered off and the resulting aqueous acid solution is gradually evaporated in a crystallizer whereupon citric acid crystallizes. Even using a modification of the lime/sulfuric process which provides for the concurrent production of citric acid and alkali citrates, (e.g., EPO,432,610), the lime/sulfuric acid process has the disadvantage of producing a vast quantity of calcium sulfate (gypsum) as a waste by-product which has to be disposed of by depositing as landfill. The latter is both expensive and an environmental problem.

While the solvent extraction process is an improvement, as it eliminates the gypsum waste product and improves process efficiency, it requires significant capital investment. Even with the additional modification to the solvent extraction process which involves subjecting a concentrated citric acid fermentation broth to solvent extraction using a recycled amine extractant, (e.g., U.S. Pat. No. 4,994,609). Not only is a large capital investment required, but special equipment is needed and organic solvents are used which require disposal.

The literature also describes other techniques for the purification of impure fermentation broth. Among the published literature is EP O 167 957, assigned to Hoechst AG, which discloses a process for isolating water soluble acidic compounds by bringing a solution of the acid into contract with a weakly basic, absorbent, ion exchange resins, preferably those containing tertiary amino groups, and then desorbing the acid by water and/or steam. This procedure is both complicated and expensive.

Offenlegungsschrift DE 3 502 924, assigned to Benckiser GmbH, discloses a citric acid purification process involving membrane filtration, preferably ultrafiltration, together with absorption on a non-ionic resin, such as polystyrene or polyacrylamide, followed by desorption and crystallization. Again the process is complicated and expensive.

U. S. Pat. No. 4,851,573, to Kulprathipanja el al, discloses a method for separation of citric acid from its fermentation broth by contacting the broth with a water-insoluble macroreticular gel of a weakly basic anionic exchange resin possessing tertiary amine groups in a cross-linked acrylic or styrene resin matrix. The citric acid is desorbed by water or dilute sulfuric acid. This method has the disadvantages of being complicated and expensive.

Juetten, in his thesis entitled "The Enhanced Crystallization of Dicarboxylic Acids in Electrolyte Solutions", Michigan State University, 1992, performed crystallization experiments on aqueous solutions using dicarboxylic acids in order to determine by trial-and-error which electrolytes caused "salting out." None of the experiments, however, were performed with a fermentation broth and the thesis does not disclose any process for the recovery of citric acid from fermentation broth using precipitation and crystal separation procedures.

In contrast to the prior art procedures for recovery of pure organic acid from an impure fermentation broth, the present invention provides a simple, cost effective process which achieves high productivity and minimal waste byproduct. All of the prior art procedures require crystallization of the organic acid after purification. Generally, the amount of crystals obtained by the prior art process is in the range of 40% to 50% and residual organic acid remains in the mother liquor, requiring recycling.

SUMMARY OF THE INVENTION

The invention provides an improved process for recovering organic acid from impure process streams, comprising: treating fermentation broth with strong acid or salt to precipitate citric acid (either before or after concentration of the fermentation broth) and then separating the citric acid crystals to recover citric acid in an amount exceeding 80%. Moreover, the process reduces impurities by 90%. Impurities are left in the residual mother liquor.

The preferred strong acid is sulfuric acid, and the recovery may be further improved by treating the mother liquor to obtain an additional yield of organic acid. A preferred treatment is a resin treatment. The mother liquor is passed through an ion exclusion resin column. This further improvement comprises the additional steps of placing the liquor separated from the organic acid crystals onto a column and eluting with water. The impurities, including the strong acid or salt thereof, are eluted before the residual organic acid. When eluted, the residual organic acid obtained is added to the separated crystals, thereby further improving the yield. If desired, the augmented acid product may be further treated by additional crystallization to provide a more highly purified acid which may be used for foods or pharmaceuticals or may be further treated by spray granulation prior to packaging.

This invention has several remarkable advantages over existing processes, including: higher productivity, simplicity, mother liquor recycle reduction, minimal reagent requirements, higher yields, decreased impurities, lower operating costs and increased product quality.

DESCRIPTION OF THE INVENTION

In accordance with applicants' discovery, the recovery of organic acid from an impure process stream can be significantly improved by treating impure stream, such as a fermentation broth (sometimes referred to as fermentation "beer"), with strong acid or salt either before or after concentration of the fermentation broth and then separating the resulting organic acid crystals to recover the desired organic acid. The biomass is generally removed by filtration prior to addition of the strong acid or salt. Concentration of the fermentation broth is accomplished by water removal techniques such as evaporation or membranes. Concentrating the impure fermentation broth is recommended to a level at least 10 percent of the saturation value at ambient temperature. The addition of a strong acid or a salt thereof causes crystallization of the organic acid in high yield. The improved process of the invention is capable of providing yields of about 80%.

After separation of the crystallized organic acid, the mother liquor, containing large amounts of strong acid, can be recycled into the process or can be run through a resin column to provide a waste stream of the added strong acid and impurities, which may be discarded, and an organic acid solution, which may be added to the separated crystals for further purification.

Residual liquors resulting from traditional organic acid recovery processes, are commonly recycled back into the process. This recycling can build up significant levels of impurities. Since various process streams have different impurities contaminating the organic acid, over time, a poor quality of organic acid may result. The process provided herein is an improvement over existing recovery processes, including the lime/sulfuric process and solvent extraction process used to recovery organic acid commercially from fermentation beer. However, the present process may be used in conjunction with these existing recovery processes to provide an improved process. In the improved process, impurities, such as color, carbonizables, other acids, such as gluconic acid, oxalic acid, phosphoric acid, hydrochloric acid, sulfuric acid and salts thereof, which are left in the residual liquor, are readily removed. The improved process recovers more organic acid from a process stream than a simple recrystallization step and provides basically a one step purification process.

Thus, the improved process of the present invention has several advantages over existing processes including: higher productivity, simplicity, reduction of process stream recycling, lower quantity of required reagents, decreased impurities (phosphite, carbonizables and color) in the recovery process and lower operating costs. The simplicity and reduction of process steps can be seen from the following chart which compares the improved process of applicants' invention with the solvent extraction process and the lime/sulfuric acid process of the prior art.

| INVENTION | SOLVENT EXTRACTION PROCESS | LIME/SULFURIC ACID PROCESS |
| --- | --- | --- |
| Fermentation Broth Concentration* | Fermentation Broth Solvent Extraction | Fermentation Broth Liming |
| Strong Acid/Salt* | Back Extraction | Filtration |
| Product Recover (>80%) | Evaporation | Acidulation |
| (Crystal Separation) | Crystallization- (30% Crystal Yield) | Filtration |
|  | Product Recovery | Evaporation |
|  |  | Crystallization- (30% Crystal Yield) |
|  |  | Product Recovery |

-continued

| INVENTION | SOLVENT EXTRACTION PROCESS | LIME/SULFURIC ACID PROCESS |
| --- | --- | --- |

*The order of the concentration step and the step of adding strong acid/salt can be reversed.

The product recovery of the invention can be further improved and made even more economical by treating the mother liquor remaining after separation of the organic acid crystals to obtain an additional yield. This can be accomplished, for example, by a resin treatment applied to the residual liquor. The resin treatment used may be in the form of an ion exchange resin column or an ion exclusion resin column. With this additional improvement, product recovery can be increased to over 90%, making the process economically viable for large scale production of citric and other organic acids which are sold as a commodity and compete worldwide on a price basis. This additional improvement provides the further advantages of: higher productivity without the requirement of additional reagents; a simpler overall process than presently utilized; a recovery process with fewer purification steps; a more flexible process without requiring regeneration; a process with a waste treatment reduction; and a process having lower operating and maintenance costs.

Organic Acids

The improved process of the invention is particularly useful for the recovery of citric acid from its fermentation broth. However, the process is applicable to other organic acids, produced by a fermentation process, including malic, itaconic and lactic acids. In addition, although the improved process is particularly useful as applied to the recovery of citric acid produced by fermentation, because of the large quantity of impurities encountered and the large scale operation usually involved, the process can also be applied to the recovery of organic acids from any impure process stream.

Strong Acids and Salts Thereof

Strong acids and salts thereof are a class of compounds (Fundamentals of Analytical Chemistry, 4th Ed., Skoog, Douglas and West, Donald, 1982, CBS College Publishing, Page 6) which ionize in a solvent to produce an electrically conducting medium. Particular examples of strong acids and salts thereof include, but are not limited to, sulfuric acid, nitric acid, hydrochloric acid, bromic acid, sodium chloride and sodium sulfate. Other strong acids and salts thereof, well known to those skilled in the art, can be used. For the process described herein, strong acids or salts chosen from the group consisting of sulfuric acid, hydrochloric acid, sodium chloride, sodium sulfate, and nitric acid are preferred. Sulfuric acid is particularly preferred.

Resin

Ion exchange resins, preferably ion exclusion resins, can optionally be used to provide an additional improvement to the recovery of the desired organic acid. Thus, it is possible to separate additional organic acid by passing the appropriate process stream to a resin column and using water to elute the acid of interest. In this process, the impurities are separated from the organic acid based on their affinity to the resin and their size. Colored impurities, salts and carbohydrates are eluted before the organic acid. The capacity of the resin is very large and, unlike resin absorption processes, no regeneration is required. An ion exclusion process is particularly beneficial since it is a continuous operation using fixed or moving columns.

The use of the improvements described above will be described in greater detail with respect to the recovery of various organic acids directly from a fermentation broth by crystallization with a strong acid or salt. The steps in one production process for citric acid includes:

1. producing a fermentation broth containing citric acid together with impurities, including a biomass residue containing a microorganism;
2. filtering the fermentation broth to substantially remove the biomass;
3. concentrating the resulting citric acid solution;
4. adding a sufficient amount of sulfuric acid to the concentrated citric acid solution to precipitate the citric acid; and
5. separating the resulting citric acid crystals from the mother liquor.

The partially purified fermentation broth, obtained after removal of the biomass, is preferably concentrated by evaporation to within about 10% of the saturation point of citric acid and most preferably to about the saturation point of citric acid.

The amount of sulfuric acid added to precipitate the citric acid is determined by the amount of the water in the fermentation broth. One skilled in the art can easily adjust the amount depending on the particular conditions and impurities in the concentrated solution.

The separated citric acid crystals are commonly washed and can optionally be further treated by (a) dissolution and recrystallization or (b) dissolution and introduction into spray granulation equipment prior to packaging.

Since competition in the production of citric acid is so intense and so price competitive, it is preferable to increase the high yield of citric acid obtained by the invention even higher by further treating the mother liquor which is separated from the crystallized citric acid. One treatment involves passing the mother liquor through a resin column, which may be an ion exclusion resin column. Strong acidic cation-exchange resins, such as sulfonated polystyrene and divinylbenzene copolymers in the proton form can be employed. The column is eluted with water at ambient temperature. The initial eluate contains sulfuric acid and other impurities such as colorants and carbohydrates. This initial eluate is combined with the water removed during the concentration of the fermentation broth. The combined waste stream may be treated and discarded. The second eluate, containing citric acid, is used to dissolve the separated citric acid crystals and then the resulting solution is treated for final recovery by crystallization or spray granulation.

The addition of strong acids or salts thereof can also be used in conjunction with other recovery processes, such as the solvent extraction or the lime/sulfuric processes. For example, a process stream produced by such recovery processes can be treated to obtain a concentrated solution of citric acid and treated by the addition of strong acid or salt. Alternatively a residual liquor, obtained after initial separation of citric acid from these recovery processes, can be treated directly by the addition of strong acid or salt if it is already sufficiently concentrated. When used with such residual liquors, it is particularly surprising that the addition of sulfuric acid will crystallize citric acid and leave other impurities in solution.

The invention is further illustrated by the following examples.

EXAMPLES

Example 1

To 100 ml (milliliters) of a saturated solution of citric acid obtained by treatment of fermentor broth at 50° C., 3 ml of sulfuric acid was added slowly. At this point, citric acid starts crystallizing. The mixture was stirred for two hours and gradually cooled to 30° C. This mixture was filtered through a buchner funnel. Eighty-three percent (83%) of citric acid was recovered. Impurities, such as carbonizables, were reduced by ninety percent (90%) and color was reduced by ninety percent (90%).

Example 2

To 100 ml of a saturated solution of citric acid obtained by evaporation of a process stream from a citric acid fermentation process at 55° C., 3 ml of sulfuric acid was added slowly. External cooling was used to prevent a rapid temperature rise of the solution. Citric acid starts to crystallize rapidly. The resulting mixture was stirred for two hours and gradually cooled to 30° C. The mixture was then filtered through a buchner funnel. Ninety-two percent (92%) of citric acid was recovered. Impurities, such as carbonizables were reduced by 90%, color was reduced by 88%, and phosphates by about 95%.

Similar results are obtained when other strong acids or salts thereof, such as nitric acid and sodium sulfate, are employed.

Example 3

A resin treatment can be applied advantageously to recover the citric acid left in the mother liquor of Example 1 to improve the overall yield of citric acid.

A column of 1.5×100 cm (centimeters) was packed with Bayer Lewatit MDS 1368 ion exclusion resin in the proton form. The mother liquor, after separation of citric acid from Example 1, was used as feed to the column. The feed was loaded on the column and water was used as the eluant. The pulse feed was 0.5 bed volume (BV) and the flow rate was 2.0 ml/min. Seventy fractions were collected on the fraction collector. The fractions were analyzed for sulfates and citric acid by high pressure liquid chromatography (PHLC). The sulfates elute earlier than citric acid which is added to the separated crystals of Example 1.

Example 4

To 20 g (grams) of fermentor beer made from dextrose fermentation by yeast (*C.guilliermondii*), 4 g of 96% sulfuric acid was added slowly. The citric acid crystals started to come out and the mixture became thick. The mixture was stirred 2 hours. The product was filtered to give citric acid.

Example 5

To 50 g of fermentor beer made from molasses fermentation by *A. niger* was slowly added 15 g of 96% sulfuric acid. The citric acid crystals started to come out and the mixture became thick. The mixture was stirred 2 hours. The product was filtered to give citric acid.

Example 6

To 16 g of fermentor beer made from molasses fermentation by yeast (*C.guilliermondii*) was added 3.2 g of 96% $H_2SO_4$. The product started to crystallize and the solution became thick. The mixture was stirred two hours. The product was filtered to give citric acid.

Example 7

To 150 g of fermentor beer made from dextrose fermentation by *A. niger* 10 g of 96% sulfuric acid was added. The mixture was then concentrated to 60% citric acid solution. The mixture (60 g) was poured into a beaker and cooled to room temperature with agitation. The crystals started to come out and the mixture became very thick. The mixture was stirred 2 hours. The product was filtered to give citric acid (97%).

Example 8

To a malic acid solution at 25° C. (90 g, 67%) was added 96% $H_2SO_4$ (18G). The reaction temperature rose to 50° C. then the product precipitated. The mixture was stirred two hours whereby the mixture temperature dropped to 25° C. The product was filtered to give malic acid.

Example 9

To an impure itaconic acid solution at 30° C. (124 g, 19%) was added 96% $H_2SO_4$(25 g). The temperature of the reaction rose to 55° C. and then the product precipitated. The mixture was stirred two hours during which time the mixture temperature dropped to 25° C. The product was filtered to give itaconic acid (84%).

It should be understood that many modifications and variations of the present invention as herein before set forth may be made without departing from the spirit and scope of thereof and therefore only such limitations should be imposed as are indicated in the appended claims.

What is claimed is:

1. A process for recovering citric acid from an impure process stream, comprising the steps of:
    a. concentrating the impure process stream to obtain a concentrated solution of citric acid;
    b. adding a sufficient amount of a strong acid or salt thereof to the concentrated solution of citric acid to crystallize citric acid; and
    c. separating the crystalized citric acid resulting from step b from the remaining concentrated solution of citric acid.

2. The process of claim 1 in which the strong acid or salt thereof is selected from the group consisting of sulfuric acid, hydrochloric acid, sodium chloride, sodium sulfate, and nitric acid.

3. The process of claim 2 in which the strong acid or salt is sulfuric acid.

4. The process of claim 1 in which the remaining concentrated solution of citric acid is treated using an ion exchange resin to recover an additional yield of citric acid.

5. The process of claim 1 in which the impure process stream is obtained from a solvent extraction process for recovering citric acid.

6. The process of claim 1 in which the impure process stream is obtained from a lime and sulphuric acid process for recovering citric acid.

\* \* \* \* \*